(12) United States Patent
Basset et al.

(10) Patent No.: US 8,039,660 B2
(45) Date of Patent: Oct. 18, 2011

(54) METHOD OF PRODUCING NITRILE COMPOUNDS

(75) Inventors: Jean-Marie Basset, Caluire et Cuire (FR); Yves Chauvin, Tours (FR); Jean-Christophe Galland, Lyons (FR); Gerald Niccolai, Villeurbanne (FR); Christine Valerio, Villeurbanne (FR); Christophe Vallee, Villeurbanne (FR)

(73) Assignee: Rhodia Polyamide Intermediates, Saint-Fons (FR)

( * ) Notice: Subject to any disclaimer, the term of this patent is extended or adjusted under 35 U.S.C. 154(b) by 257 days.

(21) Appl. No.: 12/244,233

(22) Filed: Oct. 2, 2008

(65) Prior Publication Data

US 2009/0247780 A1  Oct. 1, 2009

Related U.S. Application Data

(62) Division of application No. 10/489,838, filed as application No. PCT/FR02/03166 on Sep. 17, 2002, now abandoned.

(30) Foreign Application Priority Data

Sep. 18, 2001 (FR) ...................... 01 12040

(51) Int. Cl.
*C07C 253/10* (2006.01)
*C07C 255/03* (2006.01)
(52) U.S. Cl. .......... 558/338; 558/438; 558/439
(58) Field of Classification Search .......... 558/338, 558/438, 439
See application file for complete search history.

(56) References Cited

U.S. PATENT DOCUMENTS

| 4,087,452 A | 5/1978 | Kuntz |
| 6,197,992 B1 | 3/2001 | Fischer et al. |
| 6,469,194 B2 | 10/2002 | Burattin et al. |
| 6,559,344 B2 | 5/2003 | Mackewitz |
| 2004/0260112 A1 | 12/2004 | Basset et al. |

FOREIGN PATENT DOCUMENTS

| FR | 2 338 253 A | 8/1977 |
| FR | 2 739 378 A | 4/1997 |
| FR | 2 787 446 A | 6/2000 |
| FR | 2 829 763 A1 | 9/2001 |
| WO | WO 00 32572 | 6/2000 |

OTHER PUBLICATIONS

International Search Report for PCT/FR02/03166 dated Nov. 28, 2002.

*Primary Examiner* — James O Wilson
*Assistant Examiner* — Ebenezer O Sackey
(74) *Attorney, Agent, or Firm* — Buchanan Ingersoll & Rooney, P.C.

(57) ABSTRACT

The present invention relates to the manufacture of nitrile compounds from unsaturated organic compounds by reaction with hydrogen cyanide. It relates more particularly to the manufacture of nitrile compounds of use in the synthesis of adiponitrile, an important chemical intermediate in the manufacture of major chemical compounds, such as hexamethylenediamine and ε-caprolactam. The invention provides a process for the manufacture of organic compounds comprising at least one nitrile functional group by carrying out a hydrocyanation reaction between hydrogen cyanide and an organic compound comprising at least one ethylenic unsaturation. This reaction is carried out in the presence of a catalytic system comprising a metal element chosen from the group consisting of nickel, platinum and palladium and an organophosphorus ligand, the reaction medium additionally comprising an ionic liquid in the liquid state at least at the temperature at which the hydrocyanation reaction is carried out.

25 Claims, No Drawings

METHOD OF PRODUCING NITRILE COMPOUNDS

This application is a divisional of earlier U.S. patent application Ser. No. 10/489,838, now abandoned, filed Aug. 18, 2004, which is a National Stage of PCT/FR 02/03166, filed Sep. 17, 2002, which claims priority to FR 01/12040, filed Sep. 18, 2001, and incorporated by reference herein in their entirety.

The present invention relates to the manufacture of nitrile compounds from unsaturated organic compounds by reaction with hydrogen cyanide.

It relates more particularly to the manufacture of nitrile compounds of use in the synthesis of adiponitrile, an important chemical intermediate in the manufacture of major chemical compounds, such as hexamethylenediamine and s-caprolactam. The last two compounds are used in particular in the manufacture of polymers, such as polyamides, and more particularly polyamide-6 and polyamide-6,6, or other polymers, such as polyurethanes.

Several processes for the manufacture of nitrile compounds have been provided. Among these, the direct hydrocyanation of an olefin or polyolefin, such as, for example, 1,3-butadiene, by reaction with hydrogen cyanide is an industrially developed process which forms the subject of numerous patents or publications.

This process consists, basically, in carrying out the addition, in a first stage, of one molecule of HCN to one ethylenic unsaturation, to produce an unsaturated nitrile compound. In fact, this stage leads to the production of numerous isomers of unsaturated nitrites. The addition of a further molecule of HCN results, in a following stage, in a polynitrile, for example in a dinitrile, such as adiponitrile when the starting olefin is 1,3-butadiene.

To avoid and limit the production of byproducts not having significant use properties, the process comprises, after the first hydrocyanation stage, a stage known as the "isomerization stage", which consists in converting most of the branched nitrile isomers to linear nitrile isomers, such as, in the case of the hydrocyanation of butadiene, to 3- and 4-pentenenitriles.

These reactions are generally carried out in the liquid phase in the presence of a catalyst based on a metal, generally nickel, present in the form of a complex with an organic ligand. This reaction can be carried out in a homogeneous medium, the catalyst being soluble in the hydrocyanation medium, in particular in the olefin or the nitrites or in a third solvent. It can also be carried out with a medium exhibiting several liquid phases, the catalyst being soluble in one of the phases, more specifically in the phase formed by a polar third solvent, generally water, which phase is distinct from that formed by the olefin and the nitrites, at least at ambient temperature. The latter embodiment makes it possible to more easily extract and recover the catalyst and thus to obtain nitrile compounds comprising fewer impurities contributed by the catalyst.

These catalytic systems have been disclosed in numerous patents and several classes of ligands have been studied. The ligands are generally organophosphorus compounds, such as phosphites, phosphinites, phosphonites or phosphines. They can be monodentate or polydentate. In the case of processes in a two-phase medium, these organophosphorus ligands advantageously comprise one or more ionizable groups, such as sulphonate, phosphonate, carboxylate or ammonium groups, for example, to render them soluble in the polar phase.

Mention may be made, as example of the disclosure of these processes, of U.S. Pat. No. 3,496,217, which discloses the synthesis of adiponitrile by reaction of hydrogen cyanide with butadiene in the presence of a catalyst based on nickel complexed with a ligand, such as triaryl phosphite. This reaction is carried out with catalysis in a single-phase medium.

With regard to French Patent No. 2 338 253, it also discloses a process for the synthesis of adiponitrile by hydrocyanation of butadiene. The reaction is carried out in a two-phase liquid medium, the catalyst being present in an aqueous phase. This process makes it possible to recover the adiponitrile, devoid of catalyst and therefore of metal, in the organic phase. The catalyst disclosed is also a catalyst based on a metal, such as nickel, in combination with a ligand of the phosphine type. However, this ligand comprises sulphonate radicals, making it possible to render the catalyst soluble or dispersible in water.

Furthermore, it is also known to combine the nickel-based catalyst with promoters, such as Lewis acids, such as, for example, zinc chloride or triphenylborane, for the hydrocyanation of an unsaturated nitrile compound.

Research is continually being undertaken to improve the performance of the synthesis of nitrites by hydrocyanation, either by developing novel catalytic systems or by modifying the reaction conditions and compositions of the hydrocyanation medium.

Among the most recent patents published, U.S. Pat. No. 6,169,198 discloses the use of novel ligands of metallocene-phosphorus type. Likewise, U.S. Pat. No. 5,773,637 discloses the use, as Lewis acid, of perfluoroalkylsulphonate compounds.

One of the aims of the present invention is to provide a novel process for the manufacture of nitrites by hydrocyanation of an olefin by reaction with hydrogen cyanide which makes it possible to obtain high yields of and high selectivities for linear nitrites and an improved stability of the catalytic system.

To this end, the invention provides a process for the manufacture of organic compounds comprising at least one nitrile functional group by carrying out a hydrocyanation reaction between hydrogen cyanide and an organic compound comprising at least one ethylenic unsaturation. The latter compound will be referred to, for greater simplicity, in the present invention as an olefin or polyolefin, when it comprises several ethylenic unsaturations. However, this term "olefin" should not be interpreted as limiting the organic compounds suitable for the invention to hydrocarbons but it also relates to organic compounds comprising at least one ethylenic unsaturation and which can comprise atoms other than carbon and hydrogen or mixtures of hydrocarbons, such as the mixture obtained by distillation of oil known in the hydrocarbons field as the $C_4$ cut. This cut is advantageously treated to remove or convert impurities, such as compounds comprising an acetylenic unsaturation, for example by hydrogenation, as disclosed in U.S. Pat. No. 6,197,992. A compound will be regarded as an "olefin" within the meaning of the present invention which comprises an unsaturation and a nitrile functional group, such as, for example, the unsaturated nitrile compounds obtained by the reaction of HCN with a polyolefin.

According to one characteristic of the invention, the reaction is carried out in the presence of a catalytic system comprising a metal element chosen from the group consisting of nickel, platinum and palladium and an organophosphorus ligand, the reaction medium additionally comprising an ionic liquid which is in the liquid state at least at the temperature at which the hydrocyanation reaction is carried out.

In a first embodiment, the ionic liquid and the compound to be hydrocyanated are completely miscible, at least at the reaction temperature. The hydrocyanation reaction is carried out in a homogeneous or single-phase medium.

In a second embodiment, the ionic liquid and the compound to be hydrocyanated are immiscible or are only partially miscible at the reaction temperature. The reaction is carried out in a nonhomogeneous or two-phase medium. In this embodiment, the catalytic system is advantageously soluble in the ionic liquid.

In both these embodiments, it is possible to add a solvent of low polarity. This solvent of low polarity can be added from the beginning of the reaction but can also be used only after the end of the reaction, in order thus to promote the separation of the hydrocyanated products and of the ionic liquid, in particular in order to make possible the extraction of the catalytic system. This is because the solvent of low polarity has the role of rendering the ionic liquid insoluble in the phase composed of the said solvent, the unconverted olefin and the nitrile compounds formed.

Whatever the embodiment, it is preferable for the catalytic system to be at least partially miscible in the ionic liquid. Advantageously, this miscibility can be obtained by the presence of at least one ionizable group in the molecule of the organophosphorus ligand. Mention may be made, as ionizable groups, of groups of anionic type, such as sulphonate, phosphonate, phosphinate, carboxylate or sulphinate, or of cationic type, such as guanidinium, ammonium, pyridinium, imidazolium, phosphonium or sulphonium, for example. The number and the nature of these ionic groups are preferably chosen in order to render the ligand soluble in the ionic liquid. It can be advantageous for the nature of the ionizable group to be identical to that of the anion or of the cation associated with the ionic liquid.

The catalytic systems suitable for the invention are those which preferably comprise the element nickel in the zero oxidation state or a complex with organophosphorus ligands which can comprise several ionizable groups described above or more generally compounds comprising phosphorus capable of giving a coordination compound with transition metals and more particularly the abovementioned catalytic metals, in particular with nickel. These compounds can be mono-, bi- or polydentate and can exhibit a hydrophobic or hydrophilic nature. These compounds have been disclosed in numerous patents relating to the hydrocyanation of butadiene and belong to several classes, including in particular the organophosphites, organophosphonites, organophosphinites and organophosphines.

Such catalytic systems and their preparation processes are disclosed, for example, in French Patents 2 338 253, 2 710 909, 2 711 987, 2 739 378 and 2 778 915.

Mention may be made, as examples of organic phosphorus compounds which are suitable for the invention, of alkylphosphines, arylphosphines, alkylarylphosphines, alkyl phosphites, aryl phosphites, alkylaryl phosphites, alkylphosphinites, arylphosphinites, alkylarylphosphinites, alkylphosphonites, arylphosphonites or alkylarylphosphonites, the organic moiety of which comprises up to 36 carbon atoms and which are preferably substituted by one or more ionic groups described above.

Mention may be made, as examples of compounds, of tributylphosphine, dimethyl(n-octyl)-phosphine, tricyclohexylphosphine, triphenylphosphine, tolylphosphine, tris(p-methoxyphenyl)phosphine, diphenylethylphosphine, dimethylphenylphosphine, 1,4-bis(diphenylphosphino)butane, triethyl phosphite or diphenyl phosphite, the said compounds preferably comprising at least one ionic group described above.

Mention may be made, as examples of such compounds, of triphenylphosphine (mono meta sodium sulphate) (TPPM-SNa), (5-sodiocarboxyfur-2-yl)diphenyl-phosphine or (3-sodiosulphinatophenyl)diphenyl-phosphine.

As is disclosed in the above-mentioned patents, the catalyst can be prepared before its introduction into the medium or in situ.

For this, use is preferably made of the compounds of the metals forming the catalytic element, such as nickel, which are added to a medium in which the organophosphorus ligand is also soluble. Such a medium can be the ionic liquid. The catalytic system thus formed is added to the hydrocyanation medium.

The preferred compounds among the abovementioned compounds are those of nickel. Mention may be made, as nonlimiting examples, of:

the compounds in which the nickel is in the zero oxidation state, such as potassium tetracyano-nickelate $K_4[Ni(CN)_4]$, bis(acrylonitrile)nickel(0), bis(1,5-cyclooctadiene)nickel and derivatives comprising ligands from Group Va, such as tetrakis(triphenylphosphine)nickel (0);

the nickel compounds in which the nickel is in an oxidation state greater than zero, such as the carboxylates (in particular the acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, aryl- and alkylsulphonates, allyl or acetylacetonate.

It is not necessary for the nickel compound to be itself soluble in the preparation medium, such as the ionic liquid. This is because it is sufficient for the complex to be soluble, that is to say for the dissolution of the nickel to take place during the addition of the ligand to the ionic liquid.

When the nickel compound used corresponds to an oxidation state of the nickel greater than 0, a reducing agent for nickel which preferably reacts with the latter under the reaction conditions is added to the reaction medium. This reducing agent can be organic or inorganic or hydrogen. Mention may be made, as nonlimiting examples, of Zn powder, magnesium, $KBH_4$, $NaBH_4$ and borohydrides preferably soluble in water.

This reducing agent is added in an amount such that the number of oxidation/reduction equivalents is between 1 and 10. However, values of less than 1 and greater than 10 are not excluded.

When the nickel compound used corresponds to the 0 oxidation state of nickel, a reducing agent of the type of those mentioned above can also be added but this addition is not essential.

The same reducing agents are suitable when an iron compound is used.

In the case of palladium, the reducing agents can, in addition, be components of the reaction medium (phosphine, solvent, olefin).

According to the invention, the reaction medium comprises an ionic liquid. This ionic liquid is an ionic compound, the cation of which is of onium type having at least one heteroatom, such as N, P or S, carrying the positive charge in conjunction with a 5- or 6-membered aromatic ring, and an anion.

Such compounds are described, for example, in the article by Yves Chauvin and Hélène Olivier-Bourbigou, entitled "Nonaqueous ionic liquids as reaction solvents", published in Chemtech, 12, 1995, p. 66, the paper by T. Welton published in Chem. Rev., 1999, p. 2071, or patents, such as Patent EP 971 854.

According to a preferred characteristic of the invention, the ionic liquid comprises at least one cation chosen from the group consisting of the structures tetraalkylammonium, N-alkylimidazolium, N-alkylpyridinium, N-alkylpicolinium, N-alkyltriazolium, N-alkylfluoropyrazolium, N-pyrrolidinium, alkylsulphonium, tetraalkylphosphonium and alkyloxonium.

Mention may be made, as examples of preferred cations of the invention, of alkylimidazoliums, such as 1,3-dimethylimidazolium, 1-butyl-2,3-dimethyl-imidazolium, 1-butyl-3-methylimidazolium or 1,2,3-trimethylimidazolium.

Mention may be made, as preferred anions of the invention, of an anion chosen from halides, nitrate, phosphate, hydrosulphate, perfluoroalkyl-sulphonates, bis(perfluoroalkylsulphonyl)amides, bis(fluorosulphonyl)amide, bis(fluorophosphoryl)amide, tris(perfluoroalkylsulphonyl)methides, boron, aluminium, gallium or iron tetrahalides, phosphorus, arsenic and antimony hexahalides, zinc and tin trihalides, or copper dihalides.

The preferred anions of the invention are $Br^-$, $I^-$, $BF_4^-$, $PF_6^-$, $SbF_6^-$, $AlCl_4^-$, $ZnCl_3^-$, $SnCl_3^-$ and $(CF_3SO_2)_2N^-$.

The ionic liquid, to be suitable for the process of the invention, must be in the liquid state at least at the temperature at which the hydrocyanation reaction is carried out. However, ionic liquids which are found in the liquid state at a temperature of less than 100° C. are preferred as they make possible better separation and extraction of the catalyst from the reaction medium in the case of a two-phase system.

In addition, depending on the embodiment of the invention (single- or two-phase system), the ionic liquid which becomes miscible or at least partially miscible in the reaction medium only at the temperature at which the hydrocyanation reaction is carried out, or in the vicinity of the latter, is entirely compatible for the implementation of the invention.

In the embodiment in a two-phase medium, the immiscibility of the ionic liquid, at least at low temperature, is preferably obtained by addition to the reaction medium of a solvent of low polarity. This solvent dissolves the olefins to be hydrocyanated and the nitriles produced and renders the ionic liquid insoluble in the olefins and nitriles produced. Mention may be made, as solvent of low polarity, of saturated hydrocarbons, such as hexane, heptane, octane or toluene, or ethers, such as diethyl ether, diisopropyl ether or methyl isobutyl ether.

The conditions for carrying out the hydrocyanation reaction are described below, by way of example.

Thus, the amount of nickel compound or compound of another transition metal used is chosen in order to obtain a concentration as moles of transition metal per mole of organic compounds to be hydrocyanated or isomerized of between $10^{-4}$ and 1 and preferably between 0.005 and 0.5 mol of nickel or of the other transition metal employed.

The amount of ligand used to form the catalyst is chosen so that the number of moles of this compound with respect to 1 mol of transition metal is between 0.5 and 50 and preferably between 2 and 10.

The hydrocyanation reaction is generally carried out at a temperature of between 10° C. and 200° C. and preferably between 30° C. and 120° C.

The process of the invention can be carried out continuously or batchwise.

The hydrogen cyanide employed can be prepared from metal cyanides, in particular sodium cyanide, or cyanohydrins, such as acetone cyanohydrin, or by any other known synthetic process.

The hydrogen cyanide is introduced into the reactor in the gaseous form or in the liquid form. It can also be dissolved beforehand in an organic solvent.

In the context of a batchwise implementation, it is in practice possible to charge to a reactor, purged beforehand using an inert gas (such as nitrogen or argon), either a solution comprising all or a portion of the various constituents, the transition metal compound, the possible reducing agents and solvents, or the said constituents separately. Generally, the reactor is then brought to the chosen temperature and then the compound to be hydrocyanated is introduced. The hydrogen cyanide is then itself introduced, preferably continuously and unvaryingly.

When the reaction is complete, the reaction mixture is withdrawn after cooling and the reaction products are isolated, for example by separation of the phase comprising the catalytic system and of the phase formed by the solvent of low or no polarity, the hydrocyanated products and those which have not been converted, in the case of a two-phase system. The products from the latter phase can be separated, for example by distillation. In the case of a single-phase system, other separation means can be employed, such as, for example, distillation or liquid/liquid extraction.

In the case where the product to be hydrocyanated is an unsaturated compound comprising a nitrile functional group, it is advantageous to use, with the catalytic system, a cocatalyst comprising at least one Lewis acid.

This reaction consists in particular in converting aliphatic nitriles comprising ethylenic unsaturation, in particular linear pentenenitriles, such as 3-pentenenitrile, 4-pentenenitrile and their mixtures, obtained by hydrocyanation of butadiene, to dinitriles, more specifically to adiponitrile.

These pentenenitriles can comprise amounts, generally minor amounts, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, originating from the prior reaction for the hydrocyanation of butadiene and/or from the isomerization of 2-methyl-3-butenenitrile to pentenenitriles.

The Lewis acid used as cocatalyst makes it possible in particular, in the case of the hydrocyanation of aliphatic nitriles comprising ethylenic unsaturation, to improve the linearity of the dinitriles obtained, that is to say the percentage of linear dinitriles with respect to all the dinitriles formed, and/or to increase the activity and the lifetime of the catalyst.

The term "Lewis acid" is understood to mean, in the present text, according to the usual definition, compounds which accept electron pairs.

It is possible in particular to employ the Lewis acids cited in the work edited by G. A. Olah, "Friedel-Crafts and Related Reactions", Volume I, pages 191 to 197 (1963).

The Lewis acids which can be employed as cocatalysts in the present process are chosen from the compounds of the elements from Groups Ib, IIb, IIIa, IIIb, IVa, IVb, Va, Vb, VIb, VIIb and VIII of the Periodic Table. These compounds are generally salts, in particular halides, such as chlorides or bromides, sulphates, sulphonates, halosulphonates, perhaloalkylsulphonates, in particular fluoroalkylsulphonates or perfluoroalkylsulphonates, carboxylates, phosphates, bis (perfluoroalkylsulphonyl)-amides and tris(perfluoroalkylsulphonyl)methides.

Mention may be made, as nonlimiting examples of such Lewis acids, of zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, the chlorides or bromides of rare-earth metal elements, such as lanthanum, cerium, praseodymium, neodymium, samarium, europium, gadolinium, terbium, dysprosium, hafnium, erbium, thallium, ytterbium and lutetium, cobalt chloride, ferrous chloride or yttrium chloride.

Use may also be made, as Lewis acid, of organometallic compounds, such as triphenylborane or titanium diisopropoxide. It is, of course, possible to employ mixtures of several Lewis acids.

Preference is very particularly given, among Lewis acids, to zinc chloride, zinc bromide, stannous chloride, stannous bromide, triphenylborane and zinc chloride/stannous chloride mixtures.

The choice will preferably be made of a Lewis acid having an anion identical to or of the same nature as the anion of the ionic liquid, such as, for example, zinc chloride when the ionic liquid comprises $ZnCl_3^-$ as anion, aluminium chloride when the anion of the ionic liquid is the anion $AlCl_4^-$, lanthanum tris(bistrifluoromethylsulphonylamide) when the ionic medium is composed of the bistrifluoromethylsulphonylamide anion, or neodymium tris(trifluoromethyl-sulphonate) when the anion of the ionic medium is the trifluoromethysulphonate anion. It is also possible to employ an ionic liquid composed of a mixture of polynuclear anions, such as the anion $Zn_2Cl_5^-$ and of $ZnCl_3^-$, or $Al_2Cl_7^-$ and of $AlCl_4^-$.

In a preferred embodiment of the invention, the Lewis acid will be contributed by the anion of the ionic liquid. This ionic liquid itself contributes the effect of cocatalyst to the medium.

The Lewis acid cocatalyst employed generally represents from 0.01 to 50 mol per mole of transition metal compound, more particularly of nickel compound, and preferably from 1 to 10 mol per mole.

It is also possible, under the conditions of the hydrocyanation process of the present invention and more particularly in the presence of an ionic liquid, to carry out, in the absence of hydrogen cyanide, isomerization of 2-methyl-3-butenenitrile to pentenenitriles and more generally of branched unsaturated nitriles to linear unsaturated nitriles.

The 2-methyl-3-butenenitrile subjected to isomerization according to the invention can be employed alone or as a mixture with other compounds.

Thus, 2-methyl-3-butenenitrile can be used as a mixture with 2-methyl-2-butenenitrile, 4-pentenenitrile, 3-pentenenitrile, 2-pentenenitrile, butadiene, adiponitrile, 2-methylglutaronitrile, 2-ethylsuccinonitrile or valeronitrile.

It is particularly advantageous to treat the reaction mixture originating from the hydrocyanation of butadiene by HCN according to the conditions of the invention, that is to say in the presence of an ionic liquid.

In the context of this preferred alternative form, the catalytic system being already present for the reaction for the hydrocyanation of butadiene, it is sufficient to halt any introduction of hydrogen cyanide to allow the isomerization reaction to take place.

In this alternative form, it is possible, if appropriate, to carry out a slight flushing of the reactor using an inert gas, such as nitrogen or argon, for example, in order to drive off the hydrocyanic acid which might still be present.

The isomerization reaction is generally carried out at a temperature of 10° C. to 200° C. and preferably of 60° C. to 120° C.

In the preferred case of an isomerization immediately following the reaction for the hydrocyanation of butadiene, it will be advantageous to carry out the isomerization at the temperature at which the hydrocyanation was carried out.

As for the process for the hydrocyanation of compounds comprising ethylenic unsaturation, the catalytic system used for the isomerization can be prepared before its introduction into the reaction region. It is also possible to prepare the catalytic system "in situ" by simple mixing of these various constituents. The amount of transition metal compound and more particularly of nickel compound used and the amount of ligand are the same as for the hydrocyanation reaction.

However, the preparation of dinitrile compounds by hydrocyanation of an olefin such as butadiene can be carried out using a reaction system in accordance with the invention for the stages of formation of the unsaturated nitriles and the stage of isomerization above, it being possible for the reaction for the hydrocyanation of the unsaturated nitriles to dinitriles to be carried out with a reaction system in accordance with the invention or any other catalytic system already known for this reaction.

Likewise, the reaction for the hydrocyanation of the olefin to unsaturated nitriles and the isomerization of the latter can be carried out with a reaction system different from that of the invention, the stage of hydrocyanation of the unsaturated nitriles to dinitriles being carried out with a reaction system in accordance with the invention.

The examples given below, solely by way of indication, will illustrate the invention and its advantages.

PREPARATION OF IONIC LIQUIDS

Synthesis of 1-butyl-2,3-dimethylimidazolium bis(trifluoromethylsulphonyl)amide ($BMMI^+TF_2N^-$)

40.50 g (0.215 mol) of 1-butyl-2,3-dimethyl-imidazolium chloride are dissolved in 300 ml of distilled water. 61.62 g (0.215 mol) of lithium bis(trifluoromethylsulphonyl)amide are added and the mixture is stirred under argon for 72 hours at ambient temperature. A two-phase system is formed. After extraction with 250 ml of dichloromethane, the organic phase is washed with 800 ml of water and then concentrated. The compound exists in the form of a slightly pinkish liquid which is purified by chromatography on a neutral alumina column (eluent: dichloromethane). It is then concentrated, taken up in acetonitrile in the presence of active carbon and filtered. After drying for several hours at 60° C., the compound is obtained in the form of a colourless liquid (83.78 g, 90%). The structure of this product: $C_{11}H_{17}N_3S_2O_4F_6$, is confirmed by NMR spectral analysis.

Synthesis of 1-butyl-3-methylimidazolium bis(trifluoromethylsulphonyl)amide ($BMI^+TF_2N^-$)

41.92 g (0.240 mol) of 1-butyl-3-methyl-imidazolium chloride are dissolved in 300 ml of distilled water. 69.46 g (0.242 mol) of lithium bis(trifluoromethylsulphonyl)amide are added and the mixture is stirred under argon for 90 hours at ambient temperature. A two-phase system is formed. After extraction with 250 ml of dichloromethane, the organic phase is washed with 800 ml of water and then concentrated. The compound exists in the form of a slightly pinkish liquid which is purified by chromatography on a neutral alumina column (eluent: dichloromethane). It is then concentrated, taken up in acetonitrile in the presence of active carbon and filtered. After drying for several hours at 60° C., the compound is obtained in the form of a colourless liquid (81.47 g). Its structure, $C_{10}H_{15}N_3S_2O_4F_6$, was confirmed by NMR analysis.

Synthesis of 1-butyl-2,3-dimethylimidazolium hexafluorophosphate ($BMMI^+PF_6^-$)

33.37 g (0.200 mol) of sodium hexafluorophosphate and 37.50 g (0.199 mol) of 1-butyl-2,3-dimethylimidazolium chloride are dissolved in 150 ml of acetone. After vigorous stirring at ambient temperature under argon for 72 hours, the solution is filtered through celite and then concentrated. After chromatography on an alumina column (eluent: dichloromethane), the salt is taken up in acetonitrile in the presence of active carbon and filtered. Concentrating the solution gives 50.41 g (0.170 mol, 85%) of a white solid. The structure of this product, $C_9H_{17}N_2$ $PF_6$, is confirmed by NMR spectral analysis.

In the examples below, the abbreviations used have the following meanings:
cod: 1,5-cyclooctadiene
eq: equivalent
2M3BN: 2-methyl-3-butenenitrile
2M2BN: 2-methyl-2-butenenitrile
3PN: 3-pentenenitrile
4PN: 4-pentenenitrile
3+4PN: 3PN+4PN
DN: ADN+MGN+ESN
MGN: methylglutaronitrile
ESN: ethylsuccinonitrile
DC(Y): degree of conversion of the product Y to be hydrocyanated, corresponding to the ratio of the number of moles of Y converted to the number of starting moles of Y
TY (X): true yield of the compound X, corresponding to the ratio of the number of moles of X formed to the maximum number of moles of X
YD (X): selectivity for the compound X, corresponding to the ratio of TY (X) to DC(Y)
L: linearity: $YD_{AdN}/YD_{DN}$
GC: gas chromatography
TPPMSNa: sodium triphenylphosphate
P(Ph)$_2$PhSO$_2$Na: (3-sodiosulphinatophenyl)diphenylphosphine
P(Ph)$_2$FuCO$_2$Na: (5-sodiocarboxyfur-2-yl)diphenylphosphine
BPh$_3$: triphenylborane
In (CF$_3$SO$_3$)$_3$
ZnPh$_2$
Zn(CF$_3$SO$_3$)$_2$ Isomerization of 2-Methyl-3-Butenenitrile (2M3BN) to Linear Pentenenitriles The tests were carried out according to the following procedure and in a "Radleys" parallel reactor which makes possible simultaneous stirring and simultaneous reflux of 12 glass tubes known as Schlenk tubes.

The following are introduced successively and under argon into a glass tube:
10 mg (0.036 mmol, 1 equivalent) of Ni(COD)$_2$
66 mg (0.18 mmol, 5 equivalents) of TPPMSNa
1.5 g of ionic liquid
400 mg (4.93 mmol, 137 equivalents) of 2M3BN.

The solution is stirred at ambient temperature for 10 minutes and then 1.2 ml of heptane are added in order to obtain a two-phase reaction medium.

The tube is closed, then stirred and heated at 100° C. for 3 hours with head cooling. At the end of the reaction, the tubes are cooled in liquid nitrogen. A known amount of butylbenzene (approximately 40 mg, to act as chromatography internal standard) is added to the two-phase reaction medium, which is diluted and homogenized by the addition of 10 ml of THF. The solution obtained is filtered through a short silica column and injected in gas chromatography (GC).

In the tests carried out according to the above procedure, the starting materials comprise 2M3BN and other products. The molar formulation of these products is given in Table I below (the main components are shown).

TABLE I

| Component | Abbreviation | Mol % |
|---|---|---|
| 2-Methyl-3-butenenitrile | 2M3BN | 79 |
| 2-Methyl-2-butenenitrile | 2M2BN | 12.70 |
| 2-Pentenenitrile | 2PN | 6.30 |
| 4-Pentenenitrile | 4PN | 0 |
| 3-Pentenenitrile | 3PN | 1.30 |

The results obtained with various salts are collated in Table II below. By way of comparison, a test was carried out with a catalyst based on nickel and on a ligand, triphenylphosphine, in a single-phase medium.

TABLE II

| Ex. | Salt | DC (%) 2M3BN | YD (%) 3PN + 4PN | YD (%) 2M2BN | YD (%) 2PN | Mass balance (%) |
|---|---|---|---|---|---|---|
| A | (1) | 42 | 57 | −3.1 | 5.8 | 86 |
| 1 | [BMI] [TF$_2$N] | 95 | 90 | 2.9 | −0.4 | 96 |
| 2 | [BMMI] [PF$_6$] | 93 | 90 | 0.2 | 2.3 | 94 |
| 3 | [BMMI] [TF$_2$N] | 96 | 94 | 0.8 | 1.6 | 98 |

(1) comparative test without ionic liquid with triphenylphosphine as ligand

Tests were carried out without using a nonpolar solvent, such as heptane, in order to obtain a single-phase system. The procedure used is identical to that described above, with the exception of the absence of nonpolar solvent. The results obtained are listed in Table III below:

TABLE III

| Ex. | Ionic liquid | Duration | DC 2M3BN | YD 3PN + 4PN | YD 2M2BN | YD 2PN | Mass balance |
|---|---|---|---|---|---|---|---|
| 4 | [BMMI] [TF$_2$N] | 3 h | 95 | 88 | −0.1 | 0.2 | 92 |
| 5 | [BMMI] [PF$_6$] | 3 h | 94 | 90 | 1.3 | 1.1 | 95 |
| 6 | [BMI] [TF$_2$N] | 3 h | 94 | 90 | 1.1 | 0.8 | 97 |

Hydrocyanation of 3PN to ADN

The following are introduced successively and under argon into a glass tube:
40 mg (0.145 mmol, 1 equivalent) of Ni(COD)$_2$
264 mg (0.72 mmol, 5 equivalents) of TPPMSNa
1.5 ml of ionic liquid or 2.1 g, if the salt is solid at ambient temperature
400 mg (4.93 mmol, 34 equivalents) of 3PN
1 equivalent of Lewis acid.

The tube is closed with a stopper fitted with a septum. The reaction mixture is stirred and heated at 70° C. for 3 hours, during which period acetone cyanohydrin is slowly added (flow rate 0.12 ml/h, 0.36 ml, 3.95 mmol, 27 equivalents).

At the end of the reaction, 15 ml of acetone are added to the tube, which has been cooled to ambient temperature. The solution is stirred for 10 minutes and then poured into a flask containing a known amount of butylbenzene (approximately 250 mg, to act as chromatography internal standard). This solution is filtered and injected in GC.

A first series of examples was carried out using various Lewis acids. The results obtained are shown in Table IV below:

TABLE IV

| Ex. | 7 | 8 | 9 | 10 | 11 | 12 |
|---|---|---|---|---|---|---|
| Ligand | | | | TPPMSNa | | |
| Ionic liquid | | | | BMMI TF$_2$N | | |
| Lewis acid | ZnCl$_2$ | BPh$_3$ | In(CF$_3$SO$_3$)$_3$ | CoCl$_2$ | ZnPh$_2$ | Zn(CF$_3$SO$_3$)$_2$ |
| DC (in %) | 25.9 | 11.0 | 5.1 | 8.9 | 3.6 | 26.8 |
| L (in %) | 57.3 | 45.5 | 78.5 | 57.9 | 50.6 | 50.9 |
| TY (DN) (in %) | 16.0 | 6.1 | 0.9 | 3.9 | 1.8 | 13.1 |
| TY (NV) (in %) | 2.1 | 3.6 | 0.9 | 1.2 | 1.5 | 1.7 |
| Mass balance (in %) | 92.1 | 98.6 | 96.7 | 96.2 | 99.7 | 87.9 |

A second series of examples was carried out using various ionic liquids and ligands. The results obtained are shown in Table V below:

TABLE V

| Ex. | 13 | 14 | 15 | 16 | 17 |
|---|---|---|---|---|---|
| Ligands | TPPMSNa | P(Ph)$_2$PhSO$_2$Na | P(Ph)$_2$FuCO$_2$Na | TPPMSNa | P(Ph)$_2$FuCO$_2$Na |
| Ionic liquid | | BMMI TF$_2$N | | BMI TF$_2$N | BMMI PF$_6$ |
| Lewis acid | | | ZnCl$_2$ | | |
| DC 3PN (in %) | 25.9 | 5.7 | 12.1 | 32.5 | 4.5 |
| L (in %) | 57.3 | 36.6 | 19.8 | 60.0 | 16.9 |
| TY (DN) (in %) | 16.0 | 2.0 | 7.5 | 23.3 | 2.5 |
| TY (NV) (in %) | 2.1 | 1.1 | 1.3 | 2.8 | 1.1 |
| Mass balance (in %) | 92.1 | 97.4 | 96.7 | 93.5 | 99.1 |

We claim:

1. A process for the manufacture of an organic compound comprising at least one nitrile functional group by reaction between hydrogen cyanide and an organic compound comprising at least one ethylenic unsaturation, wherein said organic compound comprising at least one ethylenic unsaturation is an olefin or diolefin comprising from 3 to 12 carbon atoms, in the presence of a catalyst comprising an element selected from the group consisting of nickel, platinum and palladium and an organophosphorus ligand, said process comprising the step of carrying out said reaction in a reaction medium comprising an ionic liquid which comprises at least one cation and at least one anion and which is liquid at least at a temperature at which the reaction is carried out.

2. The process according to claim 1, wherein a solvent of low polarity is further added to the reaction medium in order to form a two-phase system.

3. The process according to claim 1, wherein the organophosphorus ligand has at least one ionizable functional group or one ionic group.

4. The process according to claim 1, wherein the ionic liquid comprises at least one cation selected from the group consisting of the structures tetraalkylammonium, N-alkylimidazolium, N-alkylpyridinium, N-alkylpicolinium, N-alkyltriazolium, N-alkylfluoropyrazolium, N-pyrrolidinium, alkylsulphonium, tetraalkylphosphonium and alkyloxonium.

5. The process according to claim 1, wherein the organophosphorus ligand is selected from the group consisting of tributylphosphine, dimethyl(n-octyl)-phosphine, tricyclohexylphosphine, triphenylphosphine, tolylphosphine, tris(p-methoxyphenyl)phosphine, diphenylethylphosphine, dimethylphenylphosphine, 1,4-bis(diphenylphosphino)butane, triethyl phosphite and diphenyl phosphite.

6. The process according to claim 1, wherein the metal element of the catalyst is nickel in the 0 or 1 oxidation state.

7. The process according to claim 1, wherein the organic compound comprising at least one ethylenic unsaturation is 1,3-butadiene.

8. The process according to claim 1, wherein the reaction is carried out at a temperature of between 10° C. and 200° C.

9. The process according to claim 1, wherein the ionic liquid comprises at least one anion selected from the group consisting of halides, nitrate, phosphate, hydrosulphate, perfluoroalkylsulphonates, bis(perfluoroalkylsulphonyl)amides, bis(fluorosulphonyl)amide, bis(fluorophosphoryl)amide, tris(perfluoroalkyl-sulphonyl)methides, boron, aluminium, gallium tetrahalides, iron tetrahalides, phosphorus hexahalides, arsenic hexahalides, antimony hexahalides, zinc trihalides, tin trihalides, and copper dihalides.

10. The process according to claim 9, wherein the anion is selected from the group consisting of Br$^-$, I$^-$, BF$^-_4$, PF$^-_6$, SbF$^-_6$, AlCl$^-_4$, ZnCl$^-_3$; SnCl$^-_3$; and (CF$_3$SO$_2$)$_2$N$^-$.

11. The process according to claim 4, wherein the cation is selected from the group consisting of 1,3-dimethylimidazolium, 1-butyl-2,3-dimethylimidazolium, 1-butyl-3-methylimidazolium and 1,2,3-trimethylimidazolium.

12. The process according to claim 1, wherein the ligand is an organophosphorus ligand selected from the group consisting of mono-dendate organophosphites, polydentate organophosphites, organophosphonites, organophosphinites and organophosphines.

13. The process according to claim 12, wherein the organophosphorus ligand comprises at least one ionic group.

14. The process according to claim 13, wherein the ionic group present in the organophosphorus ligand is a sulphonate, phosphonate, phosphinite, carboxylate or sulphinate anion.

15. The process according to claim 13, wherein the ionic group present in the organophosphorus ligand is a guanidinium, ammonium, pyridinium, imidazolium, phosphonium or sulphonium cation.

16. The process according to claim 13, wherein the organophosphorus ligand is selected from the group consisting of triphenylphosphine(mono meta sodium sulphate), (5-sodiocarboxyfur-2-yl)diphenylphosphine and (3-sodiosulphinatophenyl)diphenylphosphine.

17. The process according to claim 2, wherein the solvent of low polarity is selected from the group consisting of hexane, heptane, octane, toluene, diethyl ether, diisopropyl ether and methyl isobutyl ether.

18. The process according to claim 1, wherein the organic compound comprising at least one ethylenic unsaturation further comprises one nitrile functional group.

19. The process according to claim 18, wherein said organic compound comprising at least one ethylenic unsaturation is 3-pentenenitrile or 4-pentenenitrile.

20. The process according to claim 1, further comprising the step of isomerizing branched unsaturated nitrile compounds to linear nitrile compounds.

21. The process according to claim 20, wherein the isomerization step is carried out in the absence of hydrogen cyanide.

22. The process according to claim 20, wherein the reaction is carried out in the presence of a Lewis acid.

23. The process according to claim 22, wherein the Lewis acid is a compound comprising one of the elements from Groups Ib, IIb, IIIa, IIIb, IVa, IVb, Va, Vb, VIb, VIIb or VIII of the Periodic Table.

24. The process according to claim 23, wherein said Lewis acid compound is a halide, sulphate, sulphonate, carboxylate, phosphate, halosulphonate, perhaloalkylsulphonate, fluoroalkylsulphonate, perfluoroalkylsulphonate, bis(perfluoroalkylsulphonyl)amide, or tris(perfluoroalkylsulphonyl)methide.

25. The process according to claim 22, wherein the ionic liquid comprises an anion forming the Lewis acid.

* * * * *